(12) United States Patent
Young et al.

(10) Patent No.: US 10,219,794 B2
(45) Date of Patent: Mar. 5, 2019

(54) METHOD OF TREATING PLEURAL ABNORMALITY

(71) Applicant: National Taiwan University, Taipei (TW)

(72) Inventors: Tai-Horng Young, Taipei (TW);
Jin-Shing Chen, Taipei (TW);
Hong-Shiee Lai, Taipei (TW);
Ke-Cheng Chen, Taipei (TW);
Ya-Shuan Chou, Taipei (TW);
Yong-Chong Lin, Taipei (TW);
Hao-Ying Hsieh, Taipei (TW);
Hsu-Hsien Chang, Taipei (TW)

(73) Assignee: National Taiwan University, Taipei (TW)

( * ) Notice: Subject to any disclaimer, the term of this patent is extended or adjusted under 35 U.S.C. 154(b) by 647 days.

(21) Appl. No.: 14/805,877

(22) Filed: Jul. 22, 2015

(65) Prior Publication Data
US 2016/0022878 A1 Jan. 28, 2016

(30) Foreign Application Priority Data

Jul. 22, 2014 (TW) .............................. 103125198 A

(51) Int. Cl.
*A61L 31/06* (2006.01)
*A61L 31/04* (2006.01)
(Continued)

(52) U.S. Cl.
CPC .......... *A61B 17/0057* (2013.01); *A61L 27/18* (2013.01); *A61L 27/54* (2013.01); *A61L 27/56* (2013.01); *A61L 27/58* (2013.01); *A61B 2017/00004* (2013.01); *A61B 2017/0061* (2013.01); *A61B 2017/00575* (2013.01);
(Continued)

(58) Field of Classification Search
CPC ........ A61B 17/0057; A61B 2017/0061; A61B 2017/00597; A61B 2017/00942; A61B 2017/00575; A61B 2017/00893; A61B 2017/00004; A61B 2017/00809; A61B 2017/00884; A61B 2017/00951; A61L 27/25; A61L 27/54; A61L 27/18; A61L 2300/252; A61L 2300/402;
(Continued)

(56) References Cited

U.S. PATENT DOCUMENTS

| 2006/0116749 | A1* | 6/2006 | Willink ............. | A61M 25/0084 623/1.11 |
| 2007/0110888 | A1* | 5/2007 | Radhakrishnan ....... | A61L 31/10 427/2.1 |
| 2009/0205643 | A1* | 8/2009 | Tanaka ................... | A61K 9/007 128/200.24 |

* cited by examiner

*Primary Examiner* — Anh T Dang
(74) *Attorney, Agent, or Firm* — Hannah M. Tien

(57) ABSTRACT

The invention relates to a method of treating pleural abnormalities in a subject in need thereof, comprising the steps of: (a) attaching a biodegradable polymeric membrane onto a pleural wound to elicit fibronectin from fibroblasts to cause fibrous adhesion; and (b) securing the membrane with securement products, including sutures, staples, and sealants. The present invention also relates to a biodegradable adhesion membrane used for treating pleural abnormalities, comprising: a biodegradable base material selected from the group consisting of polycaprolactone (PCL), polylactic acid or polylactide (PLA), polyhydroxybutyrate (PHB), poly (ethylene adipate), poly(butylene adipate) (PBA), chitosan, hyaluronic acid, and polyglycolic acid (PGA); wherein the thickness of the membrane is 0.1-1 mm.

10 Claims, 8 Drawing Sheets
(3 of 8 Drawing Sheet(s) Filed in Color)

(51) Int. Cl.
  *A61B 17/00*  (2006.01)
  *A61L 27/18*  (2006.01)
  *A61L 27/54*  (2006.01)
  *A61L 27/56*  (2006.01)
  *A61L 27/58*  (2006.01)
  *A61F 2/00*   (2006.01)

(52) U.S. Cl.
  CPC .............. *A61B 2017/00597* (2013.01); *A61B 2017/00809* (2013.01); *A61B 2017/00884* (2013.01); *A61B 2017/00893* (2013.01); *A61B 2017/00942* (2013.01); *A61B 2017/00951* (2013.01); *A61F 2/0063* (2013.01); *A61F 2210/0004* (2013.01); *A61F 2250/0024* (2013.01); *A61L 2300/252* (2013.01); *A61L 2300/402* (2013.01); *A61L 2300/406* (2013.01); *A61L 2300/416* (2013.01)

(58) Field of Classification Search
  CPC ......... A61L 2300/406; A61L 2300/416; A61F 2210/0004; A61F 2250/004; A61F 2/0063
  See application file for complete search history.

METHOD OF TREATING PLEURAL ABNORMALITY

CROSS-REFERENCES TO RELATED APPLICATIONS

The present application claims priority to Taiwan Patent Application No. 103125198 filed on Jul. 22, 2014, incorporated herein by reference in its entirety.

FIELD OF THE INVENTION

The present invention relates to a method of treating pleural abnormalities, comprising using a biodegradable polymeric membrane, wherein the pleural abnormalities include a pneumothorax and a pleural effusion. The present invention also relates to a biodegradable adhesion membrane used for treating the pleural abnormalities

BACKGROUND OF THE INVENTION

A pneumothorax is an abnormal collection of air in the pleural space that causes an uncoupling of the lung from the chest wall. The main cause of the pneumothorax is lung lesions or pulmonary alveoli ruptures. When the pressure in the pleural cavity increases significantly to oppress the lung tissues, the lung partially or totally collapses which hinders the normal breathing. One of the symptoms of the pneumothorax is dyspnea that affects daily routine and sometimes may cause death.

The pneumothorax can be classified into a traumatic pneumothorax and a spontaneous pneumothorax according to the causes. The traumatic pneumothorax is usually related to trauma, for example, direct damages to the lung due to puncture wounds or indirect damages to the lung due to high impact on the chest. The spontaneous pneumothorax is a common clinical disease caused by many reasons and frequently seen after certain activities which increase the pressure in the chest suddenly and markedly, for example, coughs heavy liftings, exercises, etc. The spontaneous pneumothorax is divided into two types: a primary spontaneous pneumothorax (PSP) and a secondary spontaneous pneumothorax (SSP). The SSP is usually caused by lung diseases, e.g., asthma, pneumonia, or chronic obstructive pulmonary disease (COPD), which result in lung frailty, leading to lung lesions. However the cause of the PSP is unknown and established risk factors include male sex, smoking, and a family history of the pneumothorax.

The spontaneous pneumothorax not only affects the life quality of patients and endangers patients' lives, but also results in a waste of medical resources. Therefore, the treatments of the pneumothorax are not just simply removing the air in the pleural cavity and alleviating the symptoms but preventing pneumothorax from recurring.

There are three principles of the pneumothorax treatment: 1) to remove the air or gas abnormally collected in the pleural cavity; 2) to repair the damaged lung tissues or pulmonary alveoli; and 3) to perform pleurodesis to prevent pneumothorax from recurring. When the pneumothorax is diagnosed for the first time in a young patient, common dealing method is to remove the air abnormally collected in the pleural cavity by chest tube insertion or intercostal catheter drainage. Since these two treatments do not deal with the damaged lung tissues or pulmonary alveoli and no pleurodesis is performed, the chance of recurrence is quite high. Therefore, clinically a pleurodesis surgery is usually suggested to patients to prevent recurrence of the pneumothorax or the pleural effusion. It can be done chemically or surgically. Surgical pleurodesis involves mechanically irritating the parietal pleura, often with a rough pad, to cause the parietal pleura to be slightly inflamed. The inflamed parietal pleura tissues are covered by fibrin secreted by the body to adhere the parietalis pleura onto the visceralis pleura, causing fibrous adhesion so as to prevent the pneumothorax or the pleural effusion. Nevertheless, the pleurodesis causes dramatic pain in the affected part of patients.

Pleural effusion is an abnormal collection of fluid in the pleural space resulting from excessive fluid production, decreased absorption or both. It is the most common manifestation of pleural diseases, with etiologies ranging from cardiopulmonary disorders to symptomatic inflammatory or malignant diseases requiring urgent evaluation and treatment. Approximately 1.5 million patients are diagnosed with pleural effusions in the United States each year (Pleural Effusion, Jeffrey Rubins, MD).

The goal of the pleural treatment is to remove the fluid, to prevent the fluid from building up again, and to determine and treat the problems that cause the buildup of the fluid. Larger effusions may require insertion of an intercostal drain. Repeated effusions may require chemicals, such as bleomycin, tetracycline e.g. minocycline, povidone iodine, or a slurry of talc, or surgical pleurodesis, in which the two pleural surfaces are scarred to each other so that no fluid accumulates between them. This is a surgical procedure that involves the insertion of a chest tube which is required to stay in until the fluid drainage stops. This may take days to weeks and may require prolonged hospitalizations. If the chest tube becomes clogged, the fluid will be left behind and the pleurodesis will fail.

The instilled chemicals cause irritation between the parietal and the visceral layers of the pleura to close off the space between the parietal and the visceral layers, and to prevent the fluid from further accumulating. However, the chemicals may be accompanied by fever, pneumonia, immune rejection, acute respiratory distress syndrome (ARDS), etc.

Therefore, it is necessary to provide a treatment of the pleural abnormalities which reduces pains or infections in patients.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1:
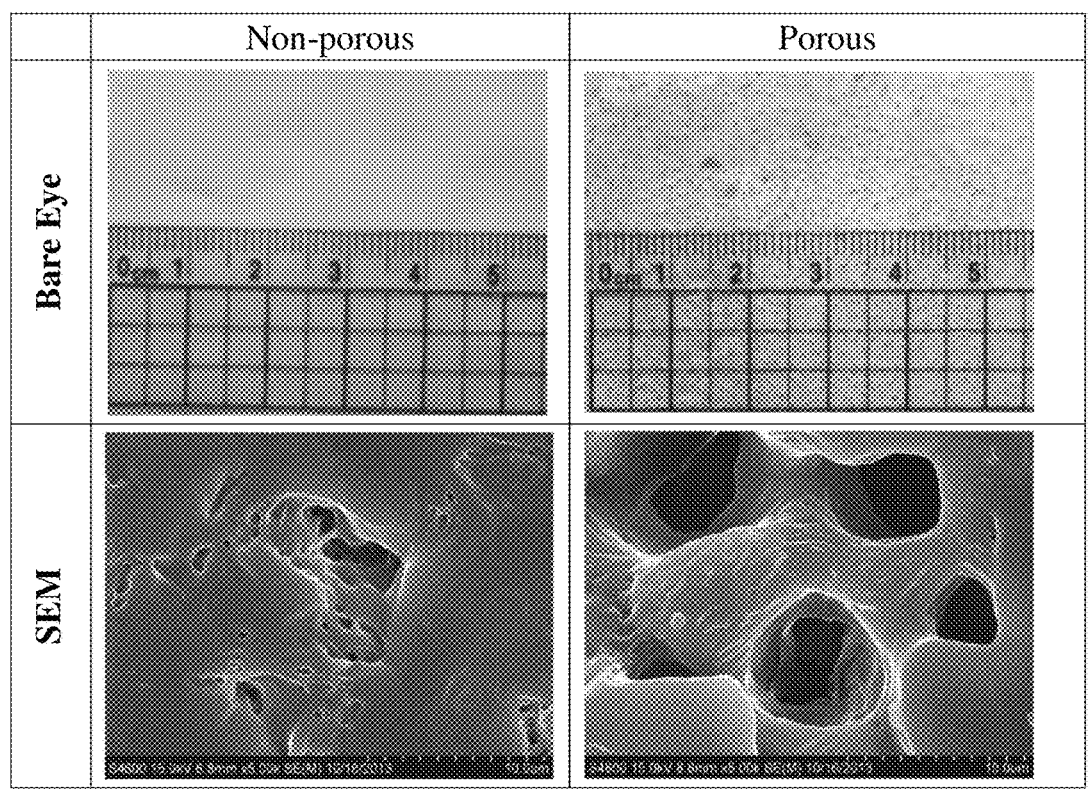
FIG. 1 shows pictures of the non-porous and the porous biodegradable polymeric membranes.

The present invention relates to a method of treating pleural abnormalities in a subject in need thereof, comprising the steps of: (a) attaching a biodegradable polymeric membrane onto a pleural wound to elicit fibronectin from fibroblasts to cause fibrous adhesion; and (b) securing the membrane with securement products, including sutures, staples, and sealants. The pleural abnormalities include a pneumothorax and a pleural effusion.

The present invention further relates to a biodegradable adhesion membrane used for treating the pleural abnormalities. The base material of the membrane is a biodegradable polymer (e.g. polycaprolactone, PCL) which is approved by the FDA to be used in human bodies. The surface of the membrane is coated with fibronectin and/or hydrophilic polymer.

DETAILED DESCRIPTION OF THE INVENTION

The detailed description provided below in connection with the appended drawings is intended as a description of the present examples and is not intended to represent the only forms in which the present example is constructed or utilized. The description sets forth the functions of the examples and the sequence of steps for constructing and operating the examples. However, the same or equivalent functions and sequences may be accomplished by different examples.

The terms "a", "an", and "the" as used herein are defined to mean "one or more" and include plural referents unless the context clearly dictates otherwise.

The present invention relates to a method of treating pleural abnormalities in a subject in need thereof, comprising the steps of: (a) attaching a biodegradable polymeric membrane onto a pleural wound to elicit fibronectin from fibroblasts to cause fibrous adhesion; and (b) securing the membrane with securement products, including sutures, staples, and sealants. The pleural abnormalities include a pneumothorax and a pleural effusion. The pleural wound includes a parietalis pleural wound and a visceralis pleural wound.

The present invention uses a biodegradable polymeric membrane to elicit extracellular matrix (such as collagen and fibronectin) from fibroblasts and the matrix accumulates on the wound, resulting in fibrous adhesion. Hence the present invention can be used for treating or inhibiting the air or fluid leakages caused by pleural lesions. The biodegradable polymeric membrane can be placed on a parietalis pleura or a visceralis pleura, or between the parietalis pleura and the visceralis pleura, to form an air-tight seal. Those patients with a pneumothorax or a pleural effusion who need the pleurodesis can use the method of the present invention to replace the surgical or the chemical pleurodesis. The biodegradable polymeric membrane can be secured with securement products, including sutures, staples, sealants, or any other common sealing materials that stays in the surgical area of the body.

The present invention also relates to a biodegradable adhesion material used for treating the pleural abnormalities. The backbone of the material is a biodegradable polymer (e.g. polycaprolactone, PCL) which is approved by the FDA to be used in human bodies. The surface of the material is coated with fibronectin and/or hydrophilic polymer. It is preferred that the material is produced in a membrane form. The length and width of the membrane is around 10 cm×10 cm, the thickness of the membrane is about 0.1-1 mm. The membrane can be cropped to at least 5 mm-2 cm larger than target wounds in size. The material is sterilized without affecting its properties and is packed individually in a sterilized package. The package should meet the following requirements: sterilization is maintained until its use, barrier is provided to prevent microbial penetration, aseptic opening is provided, the package is resistant to physical damages, compatible with sterilization processes, and complies with regulations.

The biodegradable polymeric membrane can be applied to various pleural/thoracic injuries, preferably spontaneous pneumothoraces. The biodegradable polymeric membrane also can be applied to prevent prolonged air leakages after lung surgeries.

The material of the biodegradable polymeric membrane includes but not limited to polycaprolactone (PCL), polylactic acid or polylactide (PLA), polyhydroxybutyrate (PHB), poly(ethylene adipate), poly(butylene adipate) (PBA), chitosan, hyaluronic acid, and polyglycolic acid (PGA).

The biodegradable polymeric membrane can be non-porous or porous including irregular pores. FIG. 1 shows pictures of non-porous and porous membrane; the pictures in the upper row are membranes seen by naked eyes, and the pictures in the lower row are membranes taken by a SEM.

The biodegradable polymeric materials (e.g. PCL) have been used in vivo. However, most of these materials are being surface-treated, e.g. electrical effect, to resist stickiness and adhesion. The present invent takes advantage of the stickiness property of the materials to mend the pleural tissue loss.

Figure 2:
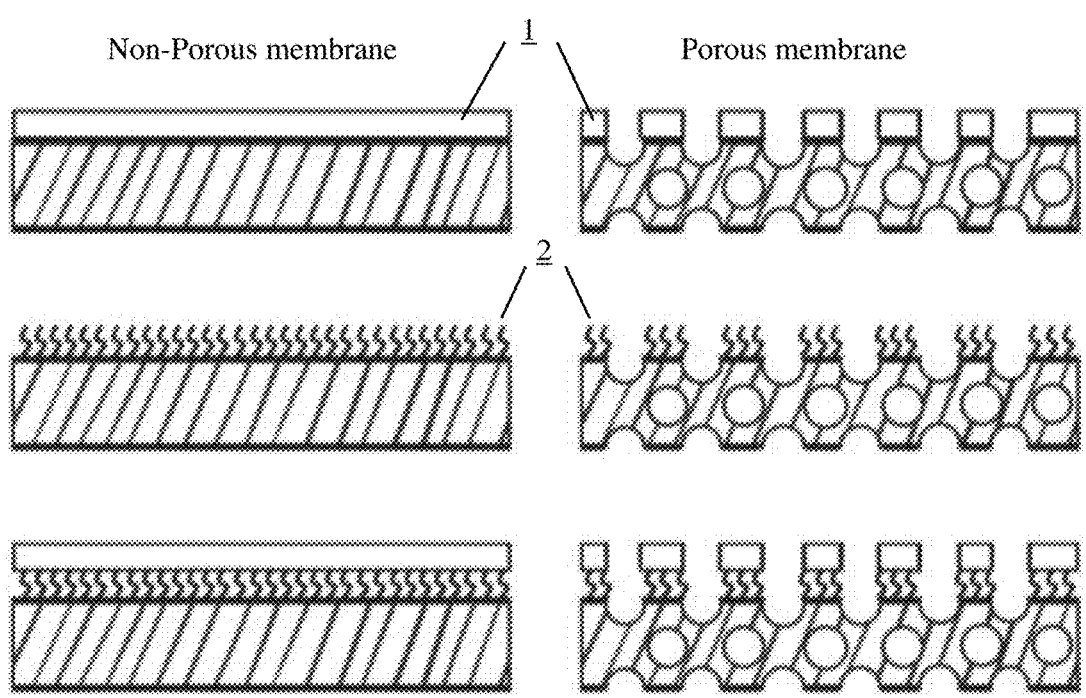
FIG. 2 shows surface modifications of the biodegradable polymeric membranes; 1: fibronectin, 2: hydrophilic polymer.

In a preferred embodiment, the surface of biodegradable polymeric membrane is coated with fibronectin. Fibronectin plays an important role in cell growth, cell adhesion, cell migration, and cell differentiation. It is also important in wound healing. While the tissue is being healed, fibroblasts secrete fibronectin and aggregate to form an insoluble matrix, resulting in fibrous adhesion. In another preferred embodiment, the biodegradable polymeric membrane is coated with hydrophilic polymer to absorb tissue fluid or pleural effusion, so that the hydrophilic polymer expands to tightly close the wound (as shown in FIG. 2).

The pore size of a porous membrane can be adjusted by manufacturing processes to conduce cell growth, and thus can achieve the effect of repairing the loss of pleura. Porous membrane has an asymmetric structure, one side of the membrane is a dense layer, and the other side is a porous layer. The dense layer binds to the pleura parietalis to stop the air or fluid leakages; and the porous layer binds to the pleura visceralis to allow cell attachment and cell growth, and to elicit the fibroblasts from defective tissues in order to secrete fibronectin. In one embodiment, the diameter of the pore is 0 (non-porous)-500 μm. In a preferred embodiment, the diameter of the pore is 0.2-20 μm. The thickness of the membrane is about 0.1-1 mm.

The biodegradable polymeric membrane is a sticky material used for repairing tissue loss. The elongation rate is no larger than 500%, and the elongation rate at break is no larger than 100%.

The concentration of the biodegradable polymeric membrane is about 5-40%. The degradation rate of the membrane can be adjusted according to the conditions of the tissue damage. Furthermore, a second surgery is not required to remove the membrane.

The biodegradable polymeric porous membrane also can carry antibiotics (e.g. Borymycin), analgesic drugs, or anti-cancer drugs (e.g. Doxorubicin, Cisplatin, 5-fluoro-uracil) to help patients recover from illness or prevent recurrence. The Borymycin can inhibit protein synthesis; therefore it can also inhibit microorganism growth. Borymycin can be used for treating diseases such as tympanitis, keratitis, pneumonia, bronchitis, urinary-tract infection, etc. Doxorubicin is a drug used in cancer chemotherapy. Cisplatin is one of the most effective broad-spectrum anticancer drugs, and also is a member of platinum-containing anti-cancer drugs. DNA is the primary target of cisplatin, and thus cisplatin not only inhibits replication and transcription of DNA, but also leads to cell apoptosis. Cisplatin is usually used in treating metastatic testis cancer, metastatic ovarian tumor, head or neck squamous cell carcinoma, bladder cancer, or thyroid cancer. 5-fluoro-uracil is an anticancer drug of a family of antimetabolites. Generally, 5-fluoro-uracil is used for treating colorectal cancer, gastric cancer, pancreas cancer, hepatoma, or bladder cancer.

The present invention uses the biodegradable polymeric membrane to elicit adhesion in pleural tissue to eliminate the air or fluid in the pleural cavity, therefore can effectively treat the pneumothorax or the pleural effusion and prevent them from recurring. The biodegradable membrane can be degraded in vivo, so that a second surgery is not required to remove the membrane. The membrane can further carry medicines and release the medicines gradually to enhance the treatment effect.

EXAMPLES

The examples below are non-limiting and are merely representative of various aspects and features of the present invention.

When performing surgery, the biodegradable polymeric membrane was attached onto the wound and its adjacent parts; for instance the surface of the liver and the parietal pleura. By attaching the membrane onto the wound, the biodegradable polymeric membrane elicited the extracellular matrix (such as collagen and fibronectin) from the fibroblasts, and then the matrix accumulated on the wound, resulting in fibrous adhesion.

Figure 3:
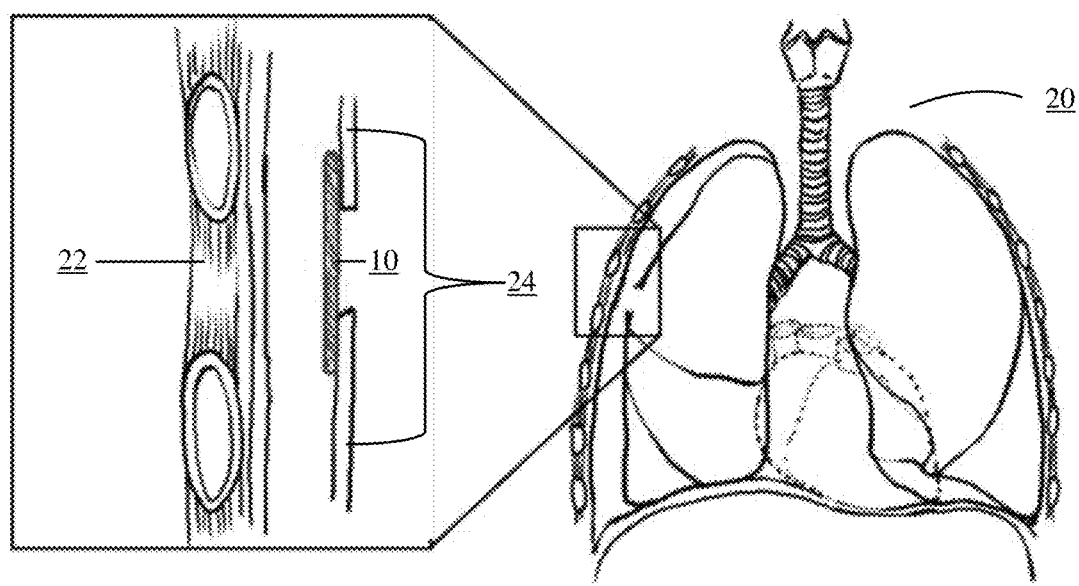
FIG. 3 shows the method of using the biodegradable polymeric membrane; 10: the biodegradable polymeric membrane, 20: the pleural cavity, 22: the parietalis pleura, 24: the visceralis pleural.

The biodegradable polymeric membrane included non-porous and porous biodegradable adhesive membrane. FIG. 3 depicted a diagram of the membrane position; number 10 indicated the biodegradable polymeric membrane. The membrane was secured on the wound with securement products, including sutures, staples, sealants, or any other surgically accepted common sealing materials that can stay in the body. The length of each side of the biodegradable polymeric membrane was 5 mm longer than the corresponding sides of the wound.

The materials of the biodegradable polymeric membrane used in the present invention included polycaprolactone (PCL), polylactic acid or polylactide (PLA), polyhydroxy-butyrate (PHB), poly(ethylene adipate), poly(butylene adipate) (PBA), chitosan, hyaluronic acid, and polyglycolic acid (PGA).

Membrane Making

To make a biodegradable polymeric membrane, the biodegradable polymeric material was dissolved in a solvent selected from a group consisting of methanoic acid, acetic acid, DMSO, and dichloromethane, to obtain a macromolecular solution of which the concentration was between 0.5-50%. The macromolecular solution was spread on a base material, e.g. glass, and added into a teflon mold to dry the base material. The base material then was neutralized by a base solution, and then was washed with deionized water. The biodegradable polymeric material was then peeled off from the base material and then was dried to form a biodegradable polymeric membrane which was capable of repairing the tissue loss.

Fibronectin Adsorption Rate

The fibronectin adsorption rate was 50-80%; preferably 70-80%. The concentration of the membrane was about 5-40%. In regard to maintain a normal human pleura thickness, the membrane thickness should be less than the normal human pleura thickness because the membrane would be thicker after the tissue become adhesive. Since the thickness of human pleura is between 1000-2000 μm, preferably the membrane thickness was about 0.1-1 mm.

To improve the treatment effect, the membrane also carried antibiotics or anticancer drugs, and gradually and properly released the drugs when the membrane was being degraded. It was noted that the types of medicines carried by a membrane were not limited to the aforementioned. Any drugs that were beneficial to treat the pleural abnormalities were eligible to be carried by the membrane.

Figure 4:
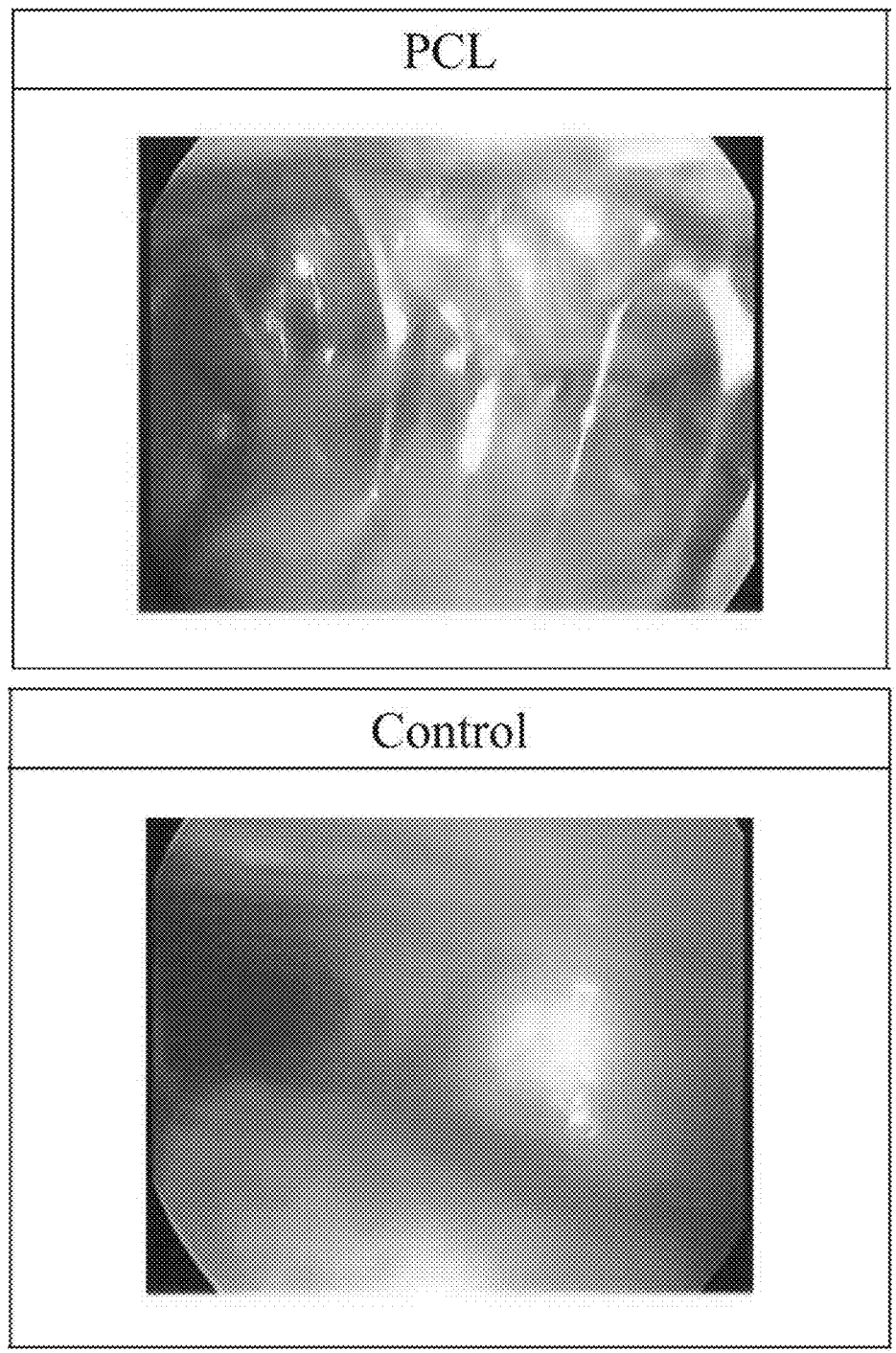
FIG. 4 shows the adhesion effect of the PCL membrane; PCL: the tissue adhesion effect with the PCL membrane, control: the tissue adhesion effect without the PCL membrane.

Non-porous membrane also had the capability of bringing adhesion effect to prevent air or fluid leakages. As shown in FIG. 4, "PCL" was the group given the PCL membrane; "Control" was the group not given any biodegradable polymeric membrane. It was evident that the control group did not show any adhesion effect while the PCL group had pronounced adhesion effect.

Fibronectin was a glycoprotein of the extracellular matrix provided for cell adhesion. Fibronectin was capable of binding extracellular matrix components such as collagen and fibrin. Fibronectin played a major role in cell adhesion, growth, migration, and differentiation, and it was also important for wound healing processes. In a preferred embodiment, different kinds of membrane were tested for the fibronectin adsorption rate. The fibronectin was prepared in a saline solution (10 mg/mL). Two milliliters of fibronectin solution was added into a dish containing the biodegradable polymeric membrane, and allowed to react at 37° C. for 1 hour. The fibronectin level adsorbed by the membrane was then examined.

The fibronectin adsorption rate of the non-porous membrane was about 60% while the adsorption rate of the porous membrane was about 70-80%. The fibronectin adsorption rate of the porous membrane with rather big pores (3-5 mm) was about 70%. The fibronectin adsorption rate of the porous membrane with irregular pores (0.1-5 mm) was about 80%. Hence, it was proved that different kinds of membrane had the capability of adsorbing the fibronectin, especially the porous membrane.

Adhesion Effect on Wound

In one embodiment, the experimental animal was anesthetized, and its abdomen was incised. The PCL membrane was then implanted into the animal's abdominal cavity, and then the incised wound was sutured. One day after the membrane implantation, the adhesion effect appeared on the test spot. About 70% of the spot surface appeared adhesion effect with respect to the non-porous membrane, and about 90% of the spot surface appeared adhesion effect with respect to the porous membrane.

Figure 5:
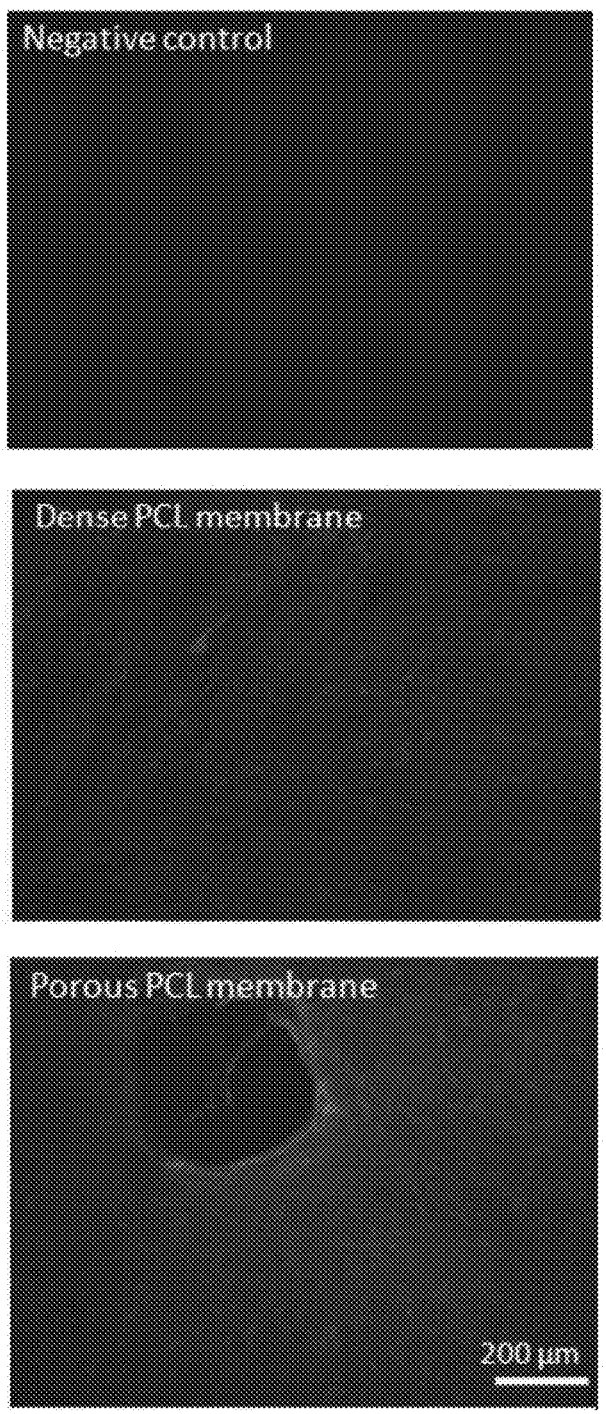
FIG. 5 shows the effect of the fibronectin level induced by the biodegradable polymeric membrane; Negative control: the fibronectin level without the PCL membrane, Dense PCL membrane: the fibronectin level induced by the non-porous PCL membrane, the porous PCL membrane: the fibronectin level induced by the porous PCL membrane.

In another embodiment, the fibronectin adsorption appeared in just 1 hour. As shown in FIG. 5, Negative control: the adsorption of the fibronectin level without the PCL membrane, Dense PCL membrane: the adsorption of the fibronectin level induced by the non-porous PCL membrane, Porous PCL membrane: the adsorption of the fibronectin level induced by the porous PCL membrane. It was noted that the adsorption of the fibronectin appeared in both non-porous and porous PCL membrane in just 1 hour.

Figure 6:
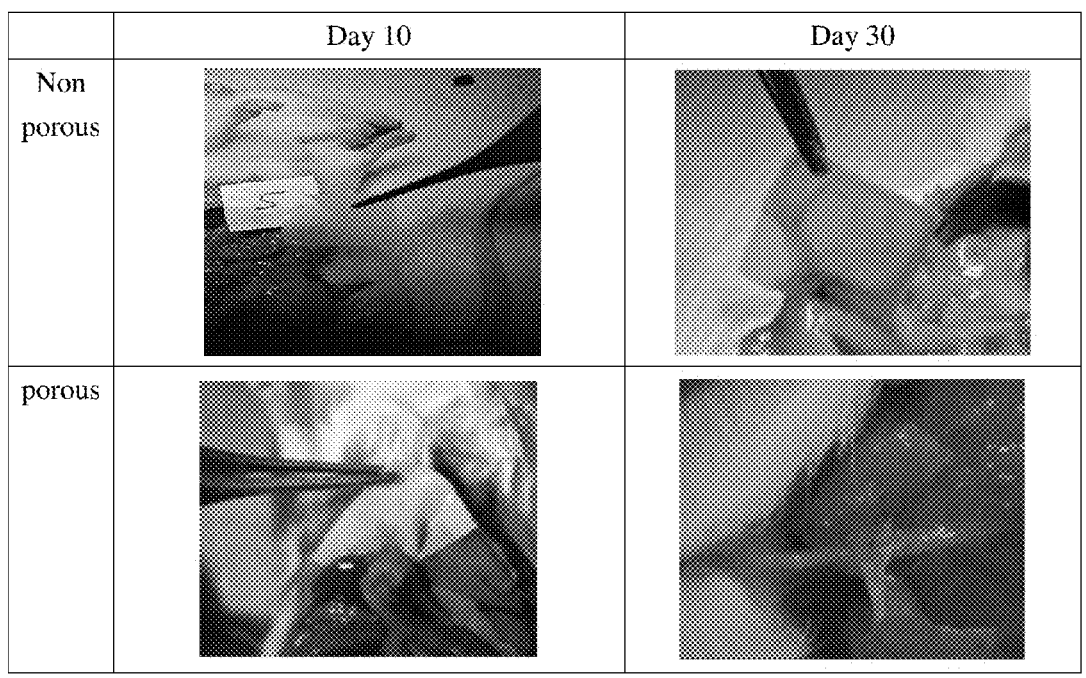
FIG. 6 shows the adhesion effect of the biodegradable polymeric membranes in animal bodies.
Figure 6:
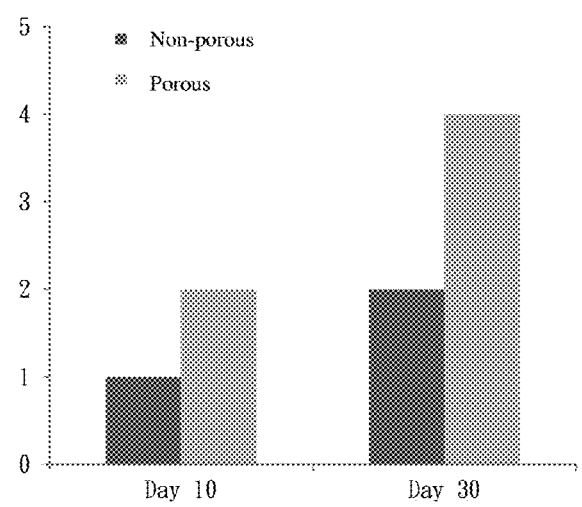

In another embodiment, the adhesion effect was observed at 10 and 30 days after the membrane implantation. The scales were defined as follows: 0: normal pleural cavity; 1: no adhesion but with a mild inflammation; 2: broad adhesion distribution (<25%); 3: generalized scattered adhesions (25-75%); 4: over-all adhesion (>75%). As shown in FIG. 6, both the non-porous and the porous membrane induced the adhesion effect, especially the porous membrane.

Tensile Strengthen Test

Figure 7:
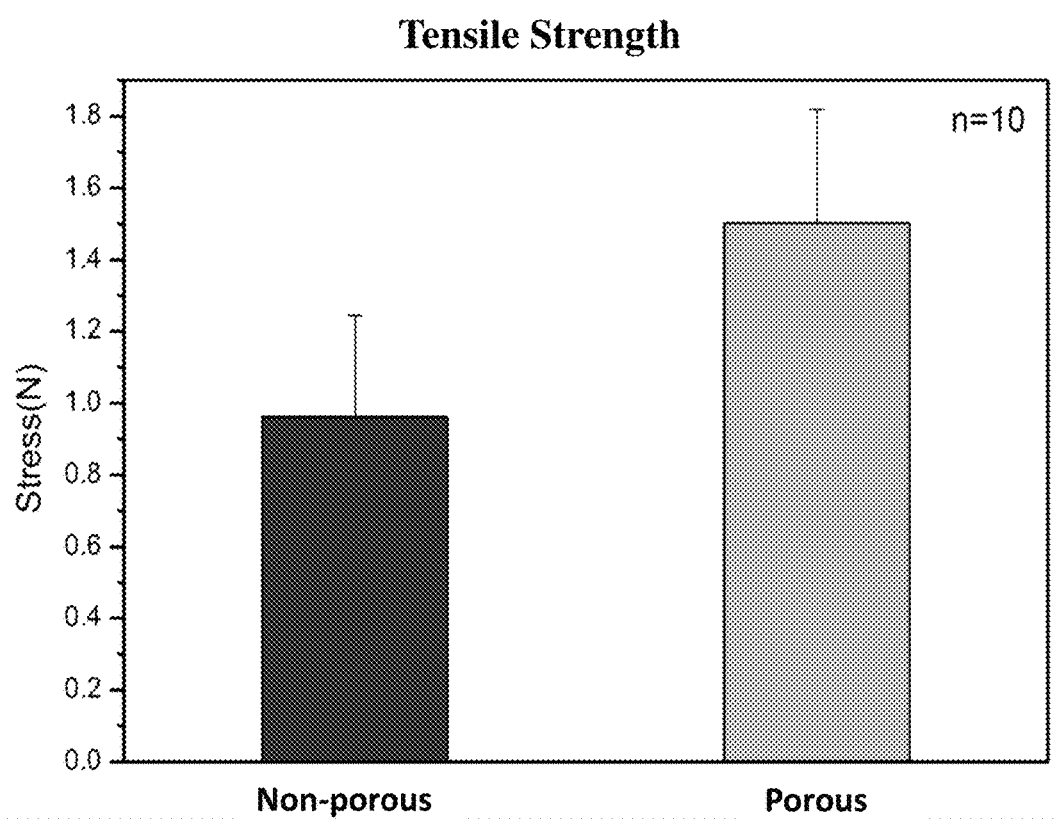
FIG. 7 shows the tensile strengthen of the biodegradable polymeric membrane.

The strength to separate a membrane and tissues was tested by a tensile strength tester. A membrane was cropped to a 1*5 mm dumbbell shape. The cropped membrane was set and fixed on the tensile strength tester, and was pulled at a tensile rates of 5 mm/min until the membrane was torn apart. The result was shown in FIG. 7. The result showed that it required 0.96 newtons (N)/cm$^2$ to break the non-porous membrane, while it required even more force (1.5 N/cm$^2$) to tear the porous membrane apart.

In another embodiment, the strength to separate the biodegradable polymeric membrane and the tissues was tested by a tensile strength tester in an animal body. The membrane was placed onto an animal wound, and then the strength to separate the membrane and wound tissue was tested 10 days after the placement. The result showed that it required about 80 N/cm$^2$ to separate the non-porous membrane from the wound tissues, while it required about 95-205 N/cm$^2$ (the forces varied according to different pore sizes or pore types) to separate the porous membrane from the wound tissues. It is understood that the biodegradable polymeric membrane and the tissues were tightly bonded; hence the membrane had the capability of preventing air or fluid leakages.

Drug Carry Test

In one embodiment, the drug release rates of different kinds of the biodegradable polymeric membrane were tested. There were 6 experimental groups and 1 control group. Control group: TCPS (Tissue Culture Polystyrene); experimental group 1: the non-porous PCL membrane without any drugs; experimental group 2: the non-porous PCL membrane with 1 µg/ml of Cisplatin (0.3 µg/well); experimental group 3: the non-porous PCL membrane with 10 µg/ml of Cisplatin (3 µg/well); experimental group 4: the porous PCL membrane without any drugs; experimental group 5: the porous PCL membrane with 1 µg/ml of Cisplatin (0.3 µg/well); and experimental group 6: the porous PCL membrane with 10 µg/ml of Cisplatin (3 µg/well). The pores of the above porous PCL membrane were created by 0.01 g/mL of NaCl.

In this embodiment, different kinds of membranes with drugs were cultured in TC-1 cell line (mouse lung cancer cell line) for three days, and the cell growth and cytotoxicity were measured by using AlamarBlue™. The absorbance was at 570 nm and 600 nm as the background.

Figure 8:
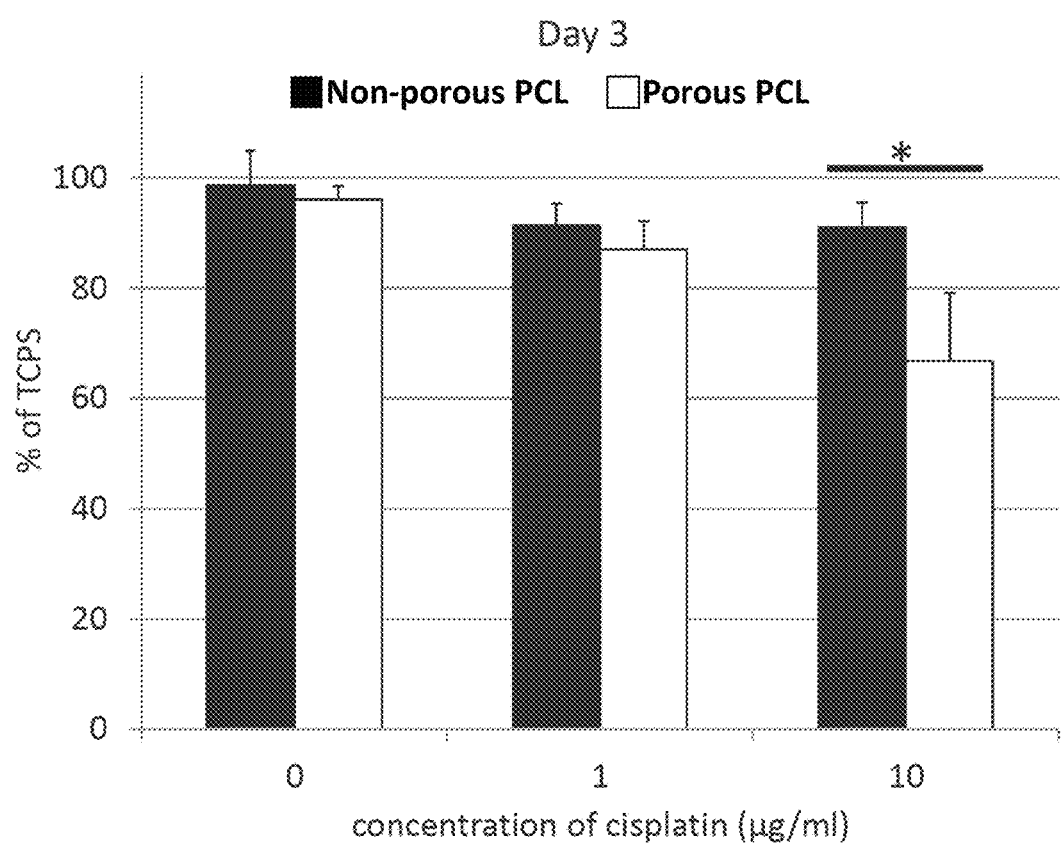
FIG. 8 shows the cytotoxicity of the non-porous or porous PCL membrane toward cancer cells with/without drugs.

As shown in FIG. 8, the cell activities cultured in the non-porous PCL membrane and the porous PCL membrane were not significantly different, indicating that both the non-porous and the porous PCL membrane were not cytotoxic. The cell activity cultured in the non-porous PCL membrane containing 10 µg/ml of cisplatin was significantly lower than that cultured in the porous PCL membrane containing 10 µg/ml of cisplatin, indicating that the drug release rate of the porous PCL membrane was faster than the drug release rate of the non-porous PCL membrane; moreover, the results also suggested that cisplatin had the capability of killing cancer cells. Thus, the result confirmed that the PCL membrane was capable of carrying drugs like cisplatin, and duly releasing those drugs which were cytotoxic.

In sum, the present invention used a non-porous or a porous biodegradable polymeric membrane as an adhesive material to treat pleural abnormalities, e.g. a pneumothorax and a pleural effusion. The membranes elicited the extracellular matrix, such as collagen or fibronectin, produced from fibroblasts to form fibrous adhesion in favor of treating or preventing air or fluid leakages caused by the loss of pleura. Compared to pleurodesis, the method of present invention did not hurt the pleura and required no second surgery to remove the membranes. Hence the method of present invention dramatically reduced patients' pain during the treatment process. In addition, the method and the membranes of the present invention provided an air-tight attachment and strong adhesion to the pleural wound, keeping the membrane stable on the wound and would not easily separate from the tissues.

The above examples are merely illustrative to explain the principles and efficacy of the present invention, and are not intended to limit the present invention. Those skilled in the art will realize that changes and modifications may be made thereto without departing from the spirit of the invention, and it is intended to include all such modifications as fall within the true scope of the invention.

What is claimed is:

1. A method of treating pleural abnormalities in a subject in need thereof, comprising the steps of:
    (a) attaching a biodegradable polymeric membrane onto a pleural wound to elicit fibronectin from fibroblasts to cause fibrous adhesion; and
    (b) securing the membrane with securement products, including sutures, staples, and sealants.

2. The method of claim 1, wherein the pleural abnormalities comprise a pneumothorax and a pleural effusion.

3. The method of claim 1, wherein the pleural wound includes a parietalis pleural wound and a visceralis pleural wound.

4. The method of claim 1, wherein the biodegradable polymeric membrane is a non-porous biodegradable polymeric membrane or a porous biodegradable polymeric membrane having a plurality of pores.

5. The method of claim 4, wherein the diameter of each pore of the porous biodegradable polymeric membrane is 0-500 µm.

6. The method of claim 1, wherein the biodegradable polymeric membrane is selected from the group consisting of polycaprolactone (PCL), polylactic acid or polylactide (PLA), polyhydroxybutyrate (PHB), poly(ethylene adipate), poly(butylene adipate) (PBA), chitosan, hyaluronic acid, and polyglycolic acid (PGA).

7. The method of claim 6, wherein the biodegradable polymeric membrane is polycaprolactone (PCL).

8. The method of claim 1, wherein the length of each side of the biodegradable polymeric membrane is at least 5 mm longer than the corresponding sides of the wound.

9. The method of claim 1, wherein the surface of the biodegradable polymeric membrane is further coated with fibronectin and/or hydrophilic polymer.

10. The method of claim 1, wherein the biodegradable polymeric membrane further carries antibiotics, analgesic drug, and/or anticancer drugs.

* * * * *